United States Patent [19]
Perrone

[11] Patent Number: 5,014,448
[45] Date of Patent: May 14, 1991

[54] POST-SURGICAL SLIPPER

[76] Inventor: Michael A. Perrone, 4103 Hillsboro Cir., Nashville, Tenn. 37215

[21] Appl. No.: 425,964

[22] Filed: Oct. 24, 1989

[51] Int. Cl.⁵ .......................... A43B 11/00; A43B 3/12
[52] U.S. Cl. ....................................... 36/110; 36/11.5; 128/83.5
[58] Field of Search .............. 36/110, 7.5, 11.5, 7.1 A, 36/7.1 R, 7.3; 128/82, 83.5

[56] References Cited

U.S. PATENT DOCUMENTS

| | | | |
|---|---|---|---|
| 3,198,192 | 8/1965 | O'brien | 128/83.5 |
| 3,566,487 | 3/1971 | Beightol | 36/110 |
| 3,661,151 | 5/1972 | Schoenbrun et al. | 128/83.5 X |
| 4,294,023 | 10/1981 | Banford | 36/11.5 |
| 4,567,678 | 2/1986 | Morgan et al. | 36/110 |
| 4,677,767 | 7/1987 | Darby | 36/110 X |
| 4,773,170 | 9/1988 | Moore et al. | 128/83.5 X |
| 4,899,468 | 2/1990 | Richbourg et al. | 128/82 X |

FOREIGN PATENT DOCUMENTS 2441350 7/1980 France .................................. 36/110

Primary Examiner—Paul T. Sewell
Assistant Examiner—Ted Kavanaugh
Attorney, Agent, or Firm—Fleit, Jacobson, Cohn, Price, Holman & Stern

[57] ABSTRACT

A slipper or article of footwear for use subsequent to surgical procedures on the foot in which immobilization is not required. The slipper includes a sole constructed of a semi-rigid material but with sufficient flexibility that a person can still walk in a normal manner. The slipper includes forward flaps which extend upwardly and over the mid-tarsal area with the toes exposed with a rear counter attached to the sole with the area covering the heel and the flaps covering the forefoot being of one-piece construction and provided with a downwardly curved juncture area with straps with hook and loop connections being crossed and connected to the flaps and opposite portions of the counter.

3 Claims, 1 Drawing Sheet

U.S. Patent  May 14, 1991  5,014,448
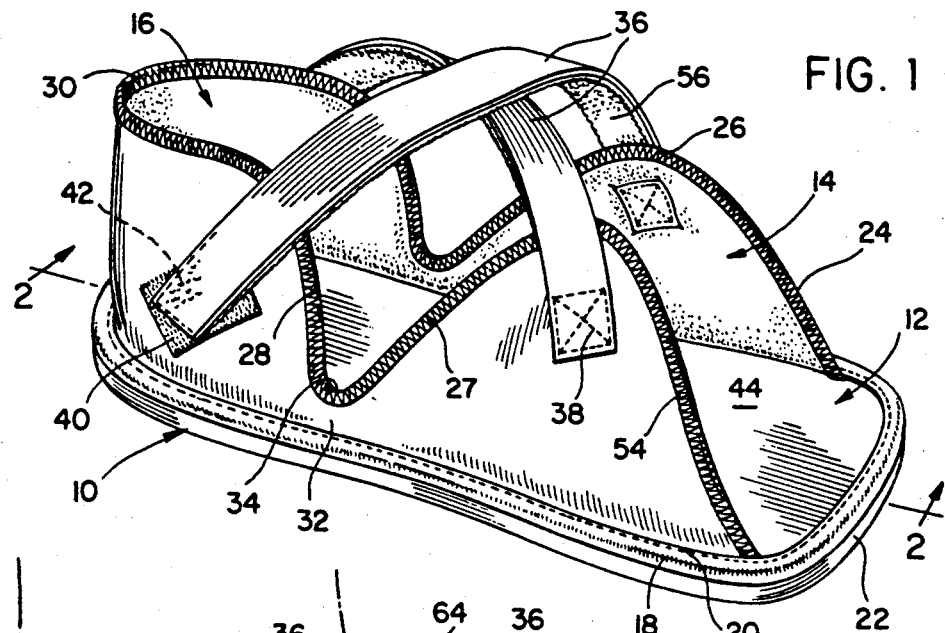
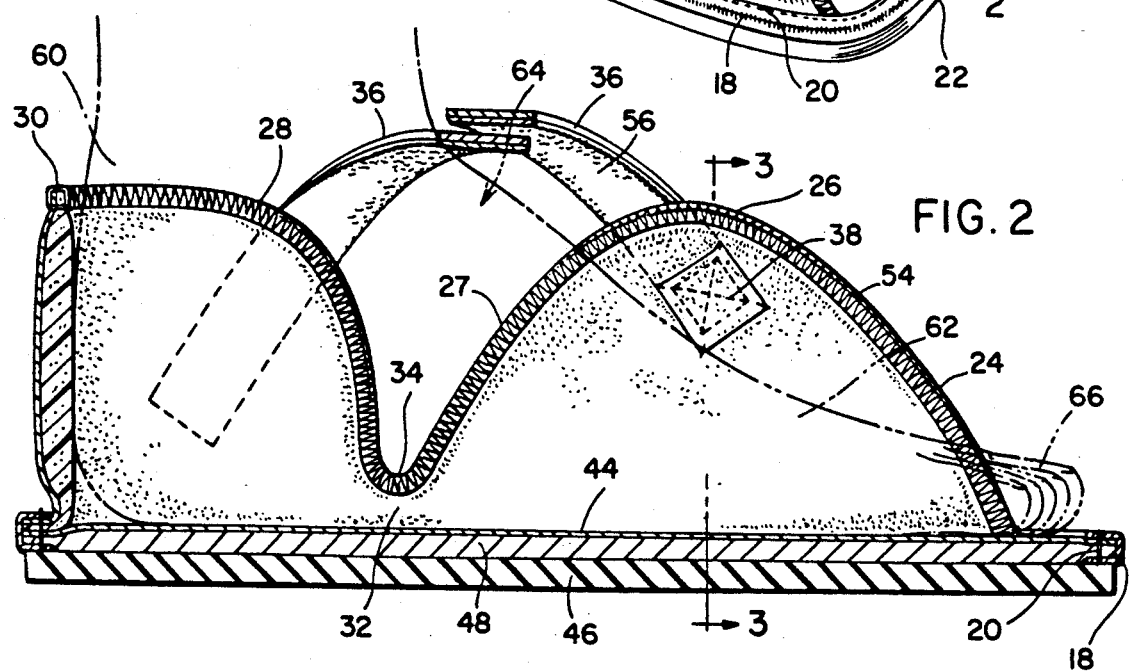
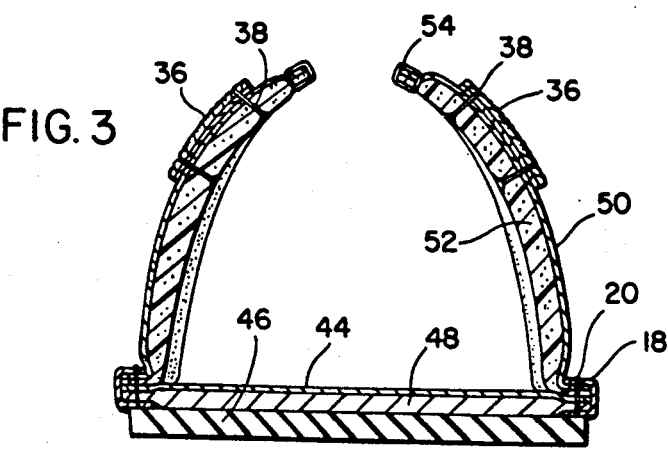

POST-SURGICAL SLIPPER

BACKGROUND OF THE INVENTION

1. Field of the Invention

The present invention generally relates to a slipper or article of footwear for use subsequent to surgical procedures on the foot in which immobilization is not required. The slipper includes a sole constructed of a semi-rigid material but with sufficient flexibility that a person can still walk in a normal manner. The slipper includes forward flaps which extend upwardly and over the mid-tarsal area with the toes exposed with a rear counter attached to the sole with the area covering the heel and the flaps covering the forefoot being of one-piece construction and provided with a downwardly curved juncture area with straps with hook and loop connections being crossed and connected to the flaps and opposite portions of the counter.

2. Information Disclosure Statement

When a patient undergoes a minor surgical procedure, the patient usually must use a paper slipper to enclose the bandaged foot or wear a conventional post-surgical shoe which provides complete rigidity or semi-rigidity to the foot. In other instances, the patient may use a conventional cut out shoe to house or receive the bandaged foot. When the procedure is scheduled in advance, the patient may bring in an old shoe to be cut out or purchase a slipper which can be cut out. The previously mentioned rigid post-surgical shoes are made of rigid wood and those that are semi-rigid are made of a rubber sole like a conventional running shoe or tennis shoe with a layer of wood laminated between the inner and outer layers. The following U.S. Pat. Nos. are relevant to surgical slippers and shoes.

4,136,468

4,677,767

While various types of footwear are known, none of the above patents or other prior art includes a flexible slipper that can be used by a patient after minor surgical procedures such as removal of ingrown toenails, planter wart excision and the like. By using the present invention, a patient undergoing such a surgical procedure will not necessarily wear a conventional rigid or semi-rigid shoe, a cut out conventional shoe or slipper, a paper slipper or a commercial slipper in which a patient must purchase a pair of slippers.

SUMMARY OF THE INVENTION

The present invention relates to a post-surgical slipper which is capable of being worn on either foot thus necessitating that a patient obtain only a single slipper which is constructed on a straight last and is universal in size with the slipper being flexible and having two flaps which extend over the mid-tarsal area to expose the toes with the flaps extending or passing over the forefoot without securement across the upper surface of the forefoot which leaves the toes exposed with the sole being sufficiently flexible and with sufficient width so as not to have the bandaged foot extend over the sole which is a common problem with conventional post-surgical shoes and shoes that are cut out that are usually pointed with commercial slippers also having the same problem.

Another object of the present invention is to provide a post-surgical slipper as set forth above in which the rear part of the slipper or counter conforms with the contour of the heel and has a forward edge which curves down to join with the downwardly curved rearward edge of the forward flaps.

A further object of the invention is to provide a post-surgical slipper having a unique structure for securing the slipper in place in which each anterior flap which extends over the mid-tarsal area are provided with a flexible strap stitched thereto in a conventional manner at a particular angle with these straps extending over the mid-foot and ankle and crossing over to give it a criss-cross or figure-8 design which enables the foot to be securely retained in the slipper without slipping and offers freedom at the toes and mid-foot with the heel being secured in a manner to prevent slipping at the heel with the criss-cross design securing the mid-foot and the forefoot with proper exposure of the forefoot for minor surgical procedures with the free ends of the straps being secured to the outer surface of the heel counter by hook and loop securing means identified by the trademark "Velcro".

Still another feature of the invention is to provide a post-surgical slipper which is simple in construction, easy to place on the foot and securely retained in position to provide a relatively inexpensive but yet comfortable slipper that can be safely worn by patients who have undergone minor surgical procedures.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the post-surgical slipper of the present invention.

FIG. 2 is a longitudinal, sectional view taken substantially upon a plane passing along section line 2–2 on FIG. 1 illustrating further structural details of the slipper.

FIG. 3 is a transverse, sectional view taken substantially upon a plane passing along section line 3–3 on FIG. 2 illustrating further structural details of the flaps which extend over the mid-tarsal area of the forefoot.

DESCRIPTION OF THE PREFERRED EMBODIMENT

Referring now specifically to the drawings, the post-surgical slipper of the present invention is generally designated by reference numeral 10 and includes a sole generally designated by the numeral 12, upwardly extending side flaps generally designated by reference numeral 14 which extend alongside of and overlie the mid-tarsal area of the foot of a patient who has undergone minor surgical procedures. The rearward portion of the slipper includes a heel enclosing area or counter 16 with the flaps and counter 16 being of one-piece construction and secured to the side edges and rear of the sole by a tape or binding 18 and stitching 20 with the binding 18 and the stitching 20 extending across the generally straight but slightly rounded toe portion 22 of the sole 12 as illustrated in FIG. 1.

Each of the flaps 14 includes a forward edge 24 which extends upwardly and rearwardly in an inclined and curved manner to a centrally disposed apex 26 and a downwardly curved rearward edge 27 which also extends rearwardly to join with the forward upwardly curved edge 28 of the counter 16 which is provided with a generally horizontally disposed top edge 30 extending around the rear surface of the heel with the flaps 14 and counter 16 being of one-piece construction with the juncture area 32 between the counter and flaps defining a generally V-shaped or U-shaped edge portion 34 as illustrated in FIGS. 1 and 2. The flaps 14 extend over the mid-tarsal area of the forefoot and each of the flaps includes a flexible strap 36 attached to the outer surface thereof by stitching 38 with the point of attachment being slightly inwardly of the apex area 26 of the flap. The straps 36 cross and the free ends thereof are adjustably connected to the outer surface of the counter 16 by a tab 40 of hook and loop pile material such as "Velcro" with the inner surface of the strap 36 also including a tab of hook and loop material 42 to cooperate with the tab 40 for adjusting the effective length of the straps 36 to securely anchor the heel counter 16 in enclosing relation to the heel and securely retain the flaps 14 across and overlying the upper surface of the mid-tarsal area of the foot with the toes of the foot exposed as illustrated in dotted line in FIG. 2.

The sole 12 includes an inner sole 44 constructed of soft, shock absorbing fabric material conventionally used in slipper construction. The bottom of the sole or outer sole is constructed of rubber, foam plastic material or similar flexible material which is resilient as designated by the numeral 46 and an intermediate stiffener 48 is provided between the outer sole and the inner sole to provide a structure for receiving the binding 18 and stitching 20 a illustrated in FIG. 3 with the sole 12 still being flexible to enable a patient to walk in a normal manner.

The shape and size of the sole 12 is such that the heel 60 and forefoot 62 of the bandaged post-surgical foot 64 will not extend over the edges of the sole and, as illustrated in FIG. 1, the shoe is constructed on a straight last and is universal in size. The upper flaps 14 and counter 16 include an outer layer 50 of fabric material and an inner layer of resilient foam plastic, rubber or the like 52 laminated thereto to provide a cushioning engagement with the surfaces of the foot which it engages. The edges of the flaps and counter may be provided with a binding, bias tape or other edging as at 54 to provide a neat appearance and to prevent the edges from becoming separated. The straps 36 are constructed of fabric material and may also be provided with a rubber or resilient liner or inner surface 56 to provide maximum comfort to the patient.

The straps 36 cross over and form a figure-8 configuration when the shoe is placed on the foot 64 with the straps 36 being adjustably connected to the outer surface of the counter 16 adjacent the lower edge portion thereof as illustrated in FIGS. 1 and 2 thereby securely retaining the counter 16 on the heel 60 so the heel does not slip and the flaps 14 retain the shoe on the mid-tarsal area 62 and secure it in place without the slipper being capable of slipping off the foot and yet offers freedom at the toes 66 and mid-foot. The freedom of the toes and mid-foot by virtue of the unique securing straps enables a patient who has undergone a minor surgical procedure to walk substantially in a conventional manner without pressure being applied to the area on which the surgical procedure was performed. The slipper can also use a strap or straps extending between the flaps and adjustably secured by "Velcro" with an ankle strap being connected to the heel counter 16. The top edges of flaps 14 will meet, overlap or be spaced apart depending on the size of the foot of the patient and additional cross straps may be added as needed.

Another embodiment of this invention is to have the sole which is flexible and of various thicknesses to be incorporated into a complete shoe with a box toe and extra depth. This shoe will be laced on the dorsum or top of the foot with laces starting at a point behind the web of the toes or it could use a tongue with flaps extending over the top of the foot and secured. The shoe is constructed for use by a patient following complete recovery of various surgical procedures or trauma such as fractures. Presently, once the patient has gone through the healing process with removal of a cast or post-surgical shoe, the patient often faces the situation of having some edema (swelling) and not being able to find a pair of conventional shoes that will fit both feet. Thus, the patient must wear mis-mated shoes. The purpose of the post-surgical ("after shoe") is to provide a patient with a straight last shoe that can be worn on either foot until complete healing takes place and conventional shoes can be worn. Also, since this shoe is an extra depth shoe, it is constructed to house an orthotic or post-surgical stabilization device made of various materials, such as an insert made of materials common in the industry, such as acrylic, leather, foam and the like. Thus, the added feature of support or stabilization is provided.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A post-surgical slipper comprising a sole constructed with sufficient flexibility to enable the sole to flex with the foot when walking normally, said sole having a constant thickness and constant flexibility characteristics throughout its length, said sole being open at the forward end and provided with flexible side edge flaps extending upwardly therefrom, said sole and flaps being symmetrically arranged in relation to a longitudinal axis to enable the slipper to be worn on either foot, said flaps having forward ends terminating adjacent to the forward end of the sole, the width and length of the sole and the position of the flaps enabling a bandaged foot to be supported without the bandaged foot extending beyond the periphery of the sole and means securing the flaps in overlying relation to the mid-tarsal area of the forefoot with the toes exposed, a heel counter of flexible construction extending upwardly from the heel portion of the sole, said heel counter being of unitary construction with the flaps, a juncture area between said side edge flaps and side portions of the heel counter, each juncture area being defined by a generally V-shaped recess extending to a point adjacent to but spaced above central side edge portions of the sole, each recess including downwardly curved convex edges on a forward edge of the heel counter and a rearward edge of the side edge flap, said convex edges diverging upwardly from a bottom apex of the recess, the bottom apex of the recess being spaced above the sole a distance substantially less than one half the height of the heel counter and flaps.

2. The structure as defined in claim 1 together with flexible straps secured to the outer surface of the flaps adjacent the upper edges thereof and means adjustably connecting the free ends of the straps to the outer surface of the heel counter.

3. The structure as defined in claim 2 wherein said means adjustably connecting the free ends of the straps to the heel counter includes coacting patches of hook and loop pile material on the heel counter and free ends of the straps.

* * * * *